(12) United States Patent
Benoit et al.

(10) Patent No.: US 8,986,734 B2
(45) Date of Patent: Mar. 24, 2015

(54) MATERIAL WITH BACTERIOSTATIC PROPERTIES

(75) Inventors: Roland Benoit, Orleans (FR); Marie-Louise Saboungi, Orleans (FR); Fabienne Brulé, Saint Denis en Val (FR)

(73) Assignees: Centre National de la Recherche Scientifique, Paris (FR); Universite d'Orleans, Orleans Cedex (FR)

( * ) Notice: Subject to any disclaimer, the term of this patent is extended or adjusted under 35 U.S.C. 154(b) by 354 days.

(21) Appl. No.: 12/865,852

(22) PCT Filed: Feb. 3, 2009

(86) PCT No.: PCT/FR2009/000120
§ 371 (c)(1),
(2), (4) Date: Nov. 16, 2010

(87) PCT Pub. No.: WO2009/109724
PCT Pub. Date: Sep. 11, 2009

(65) Prior Publication Data
US 2011/0052698 A1    Mar. 3, 2011

(30) Foreign Application Priority Data
Feb. 4, 2008  (FR) .................................. 08 00570

(51) Int. Cl.
| | |
|---|---|
| *A61K 9/14* | (2006.01) |
| *C08F 2/46* | (2006.01) |
| *A01N 59/16* | (2006.01) |
| *C08F 20/28* | (2006.01) |
| *C08J 9/00* | (2006.01) |

(52) U.S. Cl.
CPC . *C08F 2/46* (2013.01); *A01N 59/16* (2013.01); *C08F 20/28* (2013.01); *C08J 9/0066* (2013.01); *C08J 9/0071* (2013.01); *C08J 2207/10* (2013.01); *C08J 2333/06* (2013.01)
USPC .......................................................... 424/486

(58) Field of Classification Search
None
See application file for complete search history.

(56) References Cited

U.S. PATENT DOCUMENTS

2005/0013842 A1*  1/2005  Qiu et al. ...................... 424/423

FOREIGN PATENT DOCUMENTS

| EP | 1754494 A2 | 2/2007 |
| WO | WO 2005/014074 A1 | 2/2005 |
| WO | WO 2006/026026 A2 | 3/2006 |

OTHER PUBLICATIONS

Kacarevic-Popovic, Z. et al. 2007 "Radiolytic synthesis of Ag-poly(BIS-co-HEMA-co IA) nanocomposites" *Radiation Physics and Chemistry* 76: 1333-1336.

* cited by examiner

*Primary Examiner* — Dennis J Parad
(74) *Attorney, Agent, or Firm* — Knobbe, Martens, Olson & Bear, LLP

(57) ABSTRACT

The invention relates to a method for making a composite material including a porous polymer matrix containing HEMA monomers and in which silver nanoparticles are dispersed, and to the use thereof as an anti-microbial material.

8 Claims, 3 Drawing Sheets

MATERIAL WITH BACTERIOSTATIC PROPERTIES

RELATED APPLICATIONS

Figure 1:
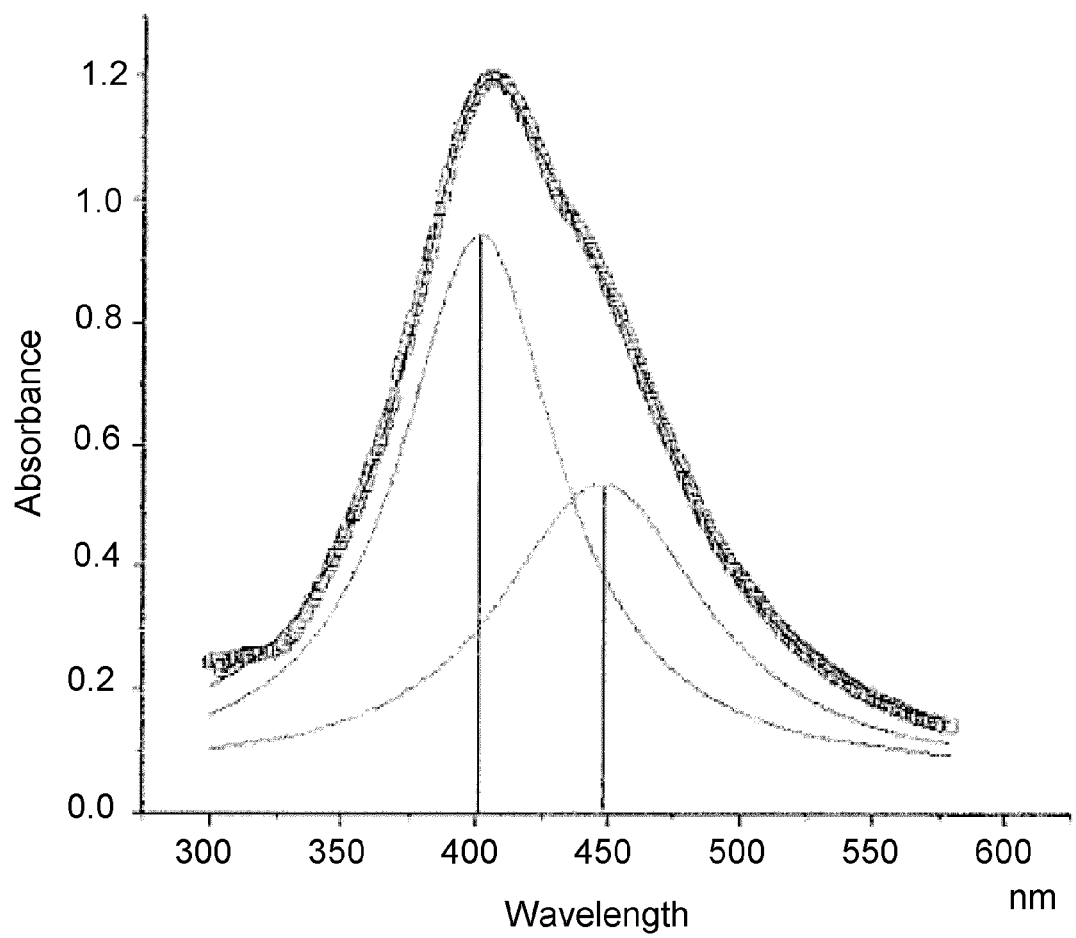

This application is a U.S. National Phase of International Application No.: PCT/FR2009/000120, filed Feb. 3, 2009, designating the U.S. and published in English on Sep. 11, 2009 as WO 2009/109724A2, which claims the benefit of French Application No. 08 00570, filed Feb. 4, 2008.

The subject of the invention is novel antimicrobial materials and a method for the production thereof.

More specifically, the invention relates to an antibacterial material comprising a porous polymer matrix in which nanoparticles of an antibacterial metal are substantially homogeneously distributed.

This material is biocompatible and enables a regular release, sustained over time, of nanoparticles of metal and of elements in ionic form, more particularly of silver, possessing antibacterial properties.

Such a material has many applications in the medical and paramedical, industrial and domestic field. In addition, it can be readily and reproducibly produced by means of a method which is simple to carry out, is readily industrializable and is economical.

Nosocomial infections are acknowledged to be a major public health problem by virtue of their frequency, their cost and their seriousness. In France, the number of patients who contract a nosocomial infection each year is estimated at between 500 000 and 800 000. This risk of infection is on average 8%, but can reach 30% in a unit such as intensive care. Antibiotics are today showing their limits in the treatment of these infections (S. V. Kyriacou, et al., *Biochemistry*, 43, (2004), 140), and it is thus necessary to limit patient contamination by reducing the proliferation of these bacteria.

Silver is a naturally bacteriostatic and fungicidal element which does not develop any habituation phenomena.

Its properties, which have been known since the earliest times (Ravelin, J. 1869. Chemistry of vegetation. Sci. Nat. 11:93-102), are based on inhibition of the reproduction of bacterial, viral and/or fungal cells. Its effectiveness is linked to its ability to be available in the form of $Ag^+$ ions (A. D. Russell, et al., *Prog Med Chem*, 31 (1994), 352; Q. L. Feng, et al., *Journal of Biomedical Materials Research*, 52, Issue 4, (2000) 662). This is why it has many applications in the form of salts.

Mention may, for example, be made of contact lenses (F. Christopher, et al., *Contact Lens & Anterior Eye* 29 (2006) 247) or dressings. However, the biological environment complexes a part of the silver ions and as a result reduces their effectiveness. Moreover, the use of more concentrated silver salts increases the risks of toxicity (Douglas Brandt B S et al., *Journal of the American Academy of Dermatology*, 53, Issue 2, (2005) S105).

In order to increase the duration of action, without increasing the ion concentration, the silver can be prepared in the form of thin films. In this case, the silver in ionic form is released by the oxidation of the surface of the deposit.

The method of production consists in covering or implanting a material with silver (G. Goshegera et al., *Biomaterials* 25 (2004) 5547) by vacuum-depositing. These methods are complex and consume energy and are therefore expensive. In addition, these materials are subject to recurring problems of adhesion or of release at the interfaces. Finally, they have the drawback of giving a small developed surface compared with the amount of silver used (Jin Wang et al., *Surface & Coatings Technology* 201 (2007) 6893). The effectiveness of these materials consequently remains low (E. P. J. M. Everaert, et al., *Journal of Materials Science—Materials in Medicine* 9 (1998), 147).

More recently, it has been proposed to use silver in the form of nanoparticles, the latter having a much lower toxicity than the salts (V. Alta et al., *Biomaterials* 25 (2004), 4383; I. Sondi et al., *Journal of Colloid and Interface Science*, 275 (2004), 177).

In the form of nanoparticles (R. Strohala et al., *Journal of Hospital Infection* (2005) 60, 226), silver has a large reactive surface area which makes it possible to optimize the release of the $Ag^+$ ions for a very small amount of material.

Recently, Jose Ruben Morones et al. (Nanotechnology 16 (2005) 2346) have shown that, under certain conditions, nanoparticles exhibit modes of action complementary to those of $Ag^+$ ions. When they are between 1 and 10 nm in size, the nanoparticles bind to the surface of cells or penetrate into said cells, destroying their capacity for reproduction.

Nanoparticles therefore represent the most effective form of silver as a bacteriostatic and fungicidal element. This form is, moreover, used in many applications (WO 2006/026026; US-2006182813; US2007218555).

However, the smaller the size of the nanoparticles, the more sensitive they are to oxidation. Produced under vacuum, they are immediately oxidized when they are exposed to air. In solution, it is imperative to use surfactants (F. Furno et al. *Journal of Antimicrobial Chemotherapy* (2004) 54, 1019) which make it possible both to control their sizes and to protect them against oxidation. However, for sizes of less than 10 nm, this protection becomes relatively ineffective and does not make it possible to preserve these nanoparticles over long periods of time. In addition to this stabilization drawback, the chemical synthesis in aqueous solution comprises many steps and generates chemical products which must be reprocessed.

Other patented methods propose incorporating these silver nanoparticles into a host material by mixing (EP-1825841). The host material effectively offers a possibility of protecting the nanoparticles against oxidation, but this method increases the production costs and the technical problems, in particular due to the inhomogeneous dispersion of the nanoparticles in the material. Finally, it is sometimes necessary, as far as possible, to perform a surface processing in order to make these compositions biocompatible.

Several methods describing the synthesis of silver nanoparticles and their inclusion in a polymer matrix are known (US-2007/0218555, US-2006/0182813, WO 2006/026026, WO 2004/002384, EP-1 825 841).

Yun-Ok Kang et al. (*Journal of Non-Cristalline Solids*, 352, Issue 5, (2006) 463) describe a material prepared in two stages: nanoparticles are coated with a polymer and then the mixture is incorporated into a second polymer obtained from aniline, a substance which is carcinogenic. The nanoparticles coated with a polymer shell are difficult to prepare, and the material is toxic, fragile and difficult to store. The method is complex and the product obtained comprises aggregates of particles distributed nonhomogeneously in the solid matrix.

F. Furno et al. (*Journal of Antimicrobial Chemotherapy*, 54 (2004) 1019) describe a long and complex method for impregnating a polymer with silver nanoparticles. The product obtained loses its bacteriostatic properties after washing.

Hyeon Suk Shin et al. (*Journal of Colloid and Interface Science*, 274 (2004) 89) describe silver nanoparticles stabilized with a polyvinylpyrrolidone coating.

V. Alt et al. (*Biomaterials*, 25 (2004) 4383) describe a poly(methyl methacrylate)-based bone cement in which silver nanoparticles are dispersed. The cement is mixed with the nanoparticles before the setting stage and is then molded and solidified.

A. M. B. Silva et al. (*Journal of Physics and Chemistry of Solids* 68 (2007) 729) describes a method in which silver salts are introduced into a resin, the resin is then crosslinked and cut up, and the silver nanoparticles are formed in situ by UV irradiation. In addition to the complexity of this method, it provides only objects of small thickness.

Document WO 2005/014074 describes contact lenses possessing antimicrobial properties, made of a polymer material in which silver nanoparticles are uniformly distributed. The polymers are based on monomers bearing siloxane functions. While they are appreciated in the ophthalmology field, these monomers are not, however, without drawbacks: the council of Europe, by virtue of its resolution ResAP (2004) 5, expresses reservations regarding contacts between siloxanes and food products, and Canada expresses reservations regarding the use of certain siloxanes and the risks that they present to human health. In addition, in polymerized form, polysiloxane has an oxygen permeability which is 12 times greater than that of pHEMA (poly(hydroxyethyl methacrylate)). In order to be effective, a bacteriostatic material containing silver nanoparticles should have a controlled size, preferably of less than 10 nm. On this scale, nanoparticles oxidize rapidly. pHEMA enables, compared with siloxane and with polysiloxane, better control of this oxidation. Finally, the authors of WO 2005/014074 have noted that, under the same conditions as those used to produce silver nanoparticles in polysiloxane, no silver nanoparticles form in hydroxyethyl methacrylate. The synthesis of these nanoparticles at the same time as that of a polymer is tricky and requires conditions that are controlled, in particular in terms of reaction medium and irradiation.

The current bacteriostatic materials are therefore relatively ineffective despite high silver salt concentrations. They generate chemical waste and/or have a high production cost owing to the numerous chemical synthesis and forming stages.

Poly(hydroxyethyl methacrylate) is particularly advantageous for all medical and paramedical applications owing to its excellent biocompatibility (M. H. Casimiro et al., *Nuclear Instruments and Methods in Physics Research B* 236 (2005) 482).

However, until very recently it was only known to combine it with silver by using the latter in the form of a salt.

The document Kacarevic-Popovic et al., Radiation Physics and Chemistry, 76 (2007), 1333-1336, describes nanocomposites of silver and of poly(BIS-co-HEMA-co-IA).

These materials are prepared by means of a three-step method:
preparation of a hydrogel of poly HEMA or of copolymer, by gamma-radiolysis of a solution of monomers,
absorption of $AgNO_3$ silver salts into the hydrogel using an aqueous solution of salts,
conversion of the silver salts into silver nanoparticles by gamma-irradiation.

In this method, the size of the nanoparticles is not controlled and a polydisperse composition of particles is obtained, the consequence of which is poor effectiveness of the product. In addition, the product obtained by means of the prior art method is very heterogeneous.

Consequently, there remains the need for a method for simply, reproducibly and economically preparing a biocompatible material, in which an antibacterial metal, such as silver, would be substantially homogeneously dispersed in the form of nanoparticles having a substantially monodisperse size distribution.

A first subject of the invention is a method for producing a composite material comprising a porous polymer matrix in which nanoparticles of an anti-bacterial metal such as silver are dispersed.

This method comprises:
(a) mixing two compositions:
 (i) a first composition comprising a polymerizable fluid comprising HEMA or 2-hydroxyethyl methacrylate, and
 (ii) a second composition comprising silver salts;
(b) irradiating the mixture of step (a) with radiation having a wavelength capable of causing the polymerization of the polymerizable fluid and the formation of silver nanoparticles.

According to the invention, the polymerizable fluid comprising HEMA comprises a mixture of monomers and/or of prepolymers capable of copolymerizing through the action of radiation having a suitable wavelength.

The HEMA is present in the polymerizable fluid in monomer or prepolymer form.

Other monomers and/or prepolymers may be present in the polymerizable fluid.

Advantageously, the comonomer(s) present in the polymerizable fluid is (are) chosen from: acrylamide, methacrylamide, $C_1$-$C_8$ dialkylacrylamides, $C_1$-$C_8$ dialkyl-methacrylamides, $C_1$-$C_8$ allylacrylamides, $C_1$-$C_8$ allyl-methacrylamides, $C_1$-$C_8$ hydroxyalkylacrylamides, $C_1$-$C_8$ hydroxyalkylmethacrylamides, N-vinyllactams, and biopolymers such as chitosan, for example.

Among the monomers which may be present together with the HEMA in the polymerizable fluid, mention may be made of hydrophilic monomers, and more particularly N,N-dimethylacrylamide (DMA), hydroxyethyl acrylate, hydroxypropyl acrylate, hydroxypropyl methacrylate, dimethylaminoethyl methacrylate (DMAEMA), dimethylaminoethylmethacrylamide, acrylamide, methacrylamide, acrylic acid, methacrylic acid and N,N-dimethyl-acrylamide.

Advantageously, the HEMA monomer or the HEMA copolymer represents more than 50% by mass of the total mass of the monomers and prepolymers of the polymerizable fluid composition, preferably more than 80%, even more preferably more than 90%, and even more advantageously more than 99%.

Advantageously, the HEMA is present in the polymerizable fluid composition in monomer form.

In addition to the monomers and/or the copolymers, the polymerizable fluid composition may comprise other constituents, such as (inorganic or polymer) fillers and solvents.

Advantageously, the addition of the following substances makes it possible, when this is desired, to obtain a monodisperse distribution of the size of the silver nanoparticles: poly (methyl methacrylate) (pMMA), polyvinylpyrrolidone, poly (acrylic acid) and poly-acrylamide. These substances are advantageously added at a molar concentration of between $10^{-6}$ and $10^{-3}$ M in the mixture of monomers and of silver salts before irradiation (the mixture of step (a)).

A polymer is a material formed by polymerization and/or crosslinking of several monomers or prepolymers.

A prepolymer is a polymer which can be further polymerized or crosslinked so as to form a polymer of higher molecular weight than the starting polymer.

The composition comprising silver salts which is used in the method of the invention is preferably an aqueous solution of silver salts. The silver salts may, for example, be $Ag_2SO_4$ or $AgNO_3$. $Ag_2SO_4$ is preferably chosen.

One or more solvents: advantageously deionized water (preferably with a conductivity of less than 18 Megohms) and at least one alcohol, are added to the mixture of the polymerizable fluid composition and of the composition comprising silver salts. Preferably, a mixture of a primary alcohol, such as ethanol or methanol, and of a secondary alcohol, such as isopropanol, is used. Advantageously, a mixture of methanol and isopropanol is used.

The mixture of step (a) preferably comprises:
55% to 70% by volume of monomer or of prepolymer,
30% to 45% by volume of solvents,
$10^{-1}$ to $10^{-5}$ percent by mass of silver salts.

Advantageously, the solvent comprises from 5% to 50% of one or more alcohols (methanol, ethanol, isopropanol) and from 95% to 50% of water.

The preferred values are:
58% to 63% and advantageously approximately 60% by volume of monomer or of prepolymer,
5% to 10% and advantageously approximately 7% by volume of methanol,
1% to 5% and advantageously approximately 3% by volume of isopropanol,
15% to 25% and advantageously approximately 20% by volume of deionized water (18 Megohms).

The constituents of the mixture are mixed and placed under an oxygen vacuum before treatment by irradiation.

This step can consist in sweeping the solution with a stream of argon, or in placing the mixture under vacuum (at a pressure of the order of 1 mbar).

The mixture of step (a) is then treated with radiation having a suitable wavelength so as to cause both the polymerization of the polymerizable fluid and the formation of silver nanoparticles. Preferably, it is a treatment with radiation having a wavelength of between $4 \times 10^{-5}$ and $10^{-12}$ meter. Advantageously, the radiation is gamma-radiation of a few picometers, from 0.5 to $2 \times 10^{-12}$ meter, even better still from 0.8 to $1.2 \times 10^{-12}$ meter, and more preferably from 0.9 to $1.1 \times 10^{-12}$ meter.

The application of this treatment to the mixture of step (a) causes the polymerization of the polymerizable mixture and the formation of silver nanoparticles simultaneously, such that a polymer matrix forms, containing a substantially uniform distribution of silver nanoparticles.

Unlike the prior art methods, the formation of the polymer and of the silver nanoparticles is simultaneous, which represents a substantial saving in terms of cost of the method. This method promotes homogeneity of the material obtained, and stabilization of the nanoparticles without the need to resort to stabilization methods such as those described in the prior art.

The controlling of the irradiation makes it possible to control the size of the nanoparticles and the polymerization kinetics. Advantageously, the dose is between 1 and 30 kGray and the dose flow rate is greater than or equal to 2 kGray/hour. Increasing the dose contributes to reinforcing the hardness of the material. Increasing the dose flow rate multiplies the number of nanoparticles, reduces their size, decreases the exposure time and increases the bacteriostatic effectiveness of the material.

When a dose flow rate of less than 2 kGray/hour is used, the bacteriostatic effectiveness of the composite material is reduced and is based essentially on the release of silver ions, since the size of the nanoparticles is predominantly greater than 10 nanometers. For a dose greater than 0.5 kGray, the composite obtained is a solid material, the yellow color of which varies according to the initial concentration of silver salts.

Advantageously, the mixture of step (a) is introduced, before irradiation, into a mold having the shape suitable for the subsequent use of the material. The irradiation results in a material of the shape and hardness selected, in which silver nanoparticles are distributed. This material is bacteriostatic and fungicidal and these properties can be observed over long periods of time.

Another subject of the invention is a composite material for which a method of preparation was described above and which comprises:
(i) a monomer-based porous polymer matrix wherein at least 50% by weight of said monomer is HEMA,
(ii) silver nanoparticles distributed in the polymer matrix.

Advantageously, the silver nanoparticles have a size of between 1 and 10 nm, advantageously between 3 and 7 nm.

Preferably, the silver nanoparticles in the material of the invention have a monodisperse size distribution. The term "monodisperse size distribution" is intended to mean a $d/d_{max}$ ratio of less than 10%, d being the diameter of any one of the nanoparticles and $d_{max}$ the diameter of the largest nanoparticle.

The silver nanoparticles are particles composed essentially of silver (Ag) having a size of less than 1 micron. The silver nanoparticles contain silver having an oxidation stage $Ag^0$, and optionally $Ag^{1+}$ and/or $Ag^{2+}$. The formation of the silver nanoparticles can be observed by UV spectrometry by means of a characteristic peak located in the wavelength range between 340 and 460 nm. For clusters of a few atoms, an absorption peak between 630 and 690 nm can also be observed.

The polymer matrix comprises pores having a size of between 1 nanometer and 5 microns, preferably between 20 nm and 1 μm, advantageously between 25 nm and 0.1 μm. The nature of the mixture of the monomers and also the irradiation flow rate (dose and dose flow rate) make it possible to control the porosity of the matrix.

The properties of the polymer matrix are controlled by the strength and the duration of the irradiation. The yellow coloration of the bacteriostatic composite material comes from the plasmon absorption of the silver nanoparticles. This absorption has been demonstrated by UV-visible spectroscopy. When the size of the nanoparticles is less than 1 nm, for example owing to a dose flow rate of greater than 2 kGray/hour, the coloration of the bacteriostatic composite material has pink as the dominant color. This coloration also comes from an absorption phenomenon due to surface plasmons.

For the same dose flow rate, the duration of the irradiation increases the degree of polymerization and/or of crosslinking of the polymer and therefore the hardness of the material.

The amount of silver in the final material is preferably between $10^{-2}$ and $10^{-5}$% by mass relative to the total mass of the material.

After irradiation, the material remains stable in air for several months. For prolonged storage, it is preferable to store it in a dry dark place.

The material of the invention can be used directly out of the mold, or else it can be milled so as to form a powder. The particle size of the powder is controlled by the hardness of the material of the invention and the milling conditions.

Depending on the intended application, the material is subjected to irradiation which gives it a high hardness (prosthesis, surgical instrument) or, on the contrary, it is subjected to a smaller amount of irradiation so as to have a certain flexibility (surgical cement, dressing, lens).

The material of the invention can be used in many applications, in the medical, cosmetics, domestic or industrial field.

In the medical field, it can be used for the manufacture of prostheses or as a cement for the implantation of prostheses, or it can be used to manufacture surgical instruments. It can be used to produce lenses, in particular post-surgical dressing lenses, or it can also be used in the manufacture of dressings to be applied to the skin and also for manufacturing implants for the diffusion of ionic silver.

The material of the invention can be used for manufacturing equipment intended for construction, for use by individuals, or for use by communities:

Antibacterial surfaces can be obtained by applying a surface coating (paint) comprising a powder of a material of the invention. Electrical switches can be molded out of a material of the invention. The internal walls of refrigerators can be molded out of a material of the invention. It is also possible to use said material for producing drinking water reservoirs.

This material also has many applications in the furniture sector: trays intended to hold surgical instruments, changing tables, bathroom or kitchen furniture, furniture intended to equip community environments such as day-nursery, hospitals, old people's homes, schools.

The material of the invention in the form of a powder can be used as a preservative in cosmetic compositions or paint compositions. It can also be part of the make-up of jars in which such compositions can be stored.

The sustained bacteriostatic and fungicidal properties of the material of the invention, combined with its good biocompatibility, enable, in all these applications, a reduction in microbial proliferation and better health safety.

The materials of the invention can not only be used for eliminating or reducing the microorganisms capable of creating health problems, but also for their bacteriostatic properties with respect to bacteria that are responsible for putrid odors.

To this effect, the materials of the invention are of use in the manufacture of clothing, of sporting equipment, of insoles for shoes, and in bathroom suites and kitchen installations.

For some applications, in particular the production of dressing lenses, the material of the invention is preferably prepared at the time of its use. Thus, another subject of the invention is a composition such as that for which a method of preparation was described above, in two parts for the extemporaneous preparation of a material of the invention and comprising at least:

(i) a first composition comprising a polymerizable fluid comprising HEMA or 2-hydroxyethyl methacrylate, and
(ii) a second composition comprising silver salts, each of these compositions having the characteristics described above.

The extemporaneous mixing of the two compositions, followed by the inserting into a mold and the gamma-irradiation, provides an article made of an antimicrobial material which is sterile and can be used directly.

EXAMPLE

FIG. 1: Differential spectrum of absorption between a composite material and a reference.

Figure 2:
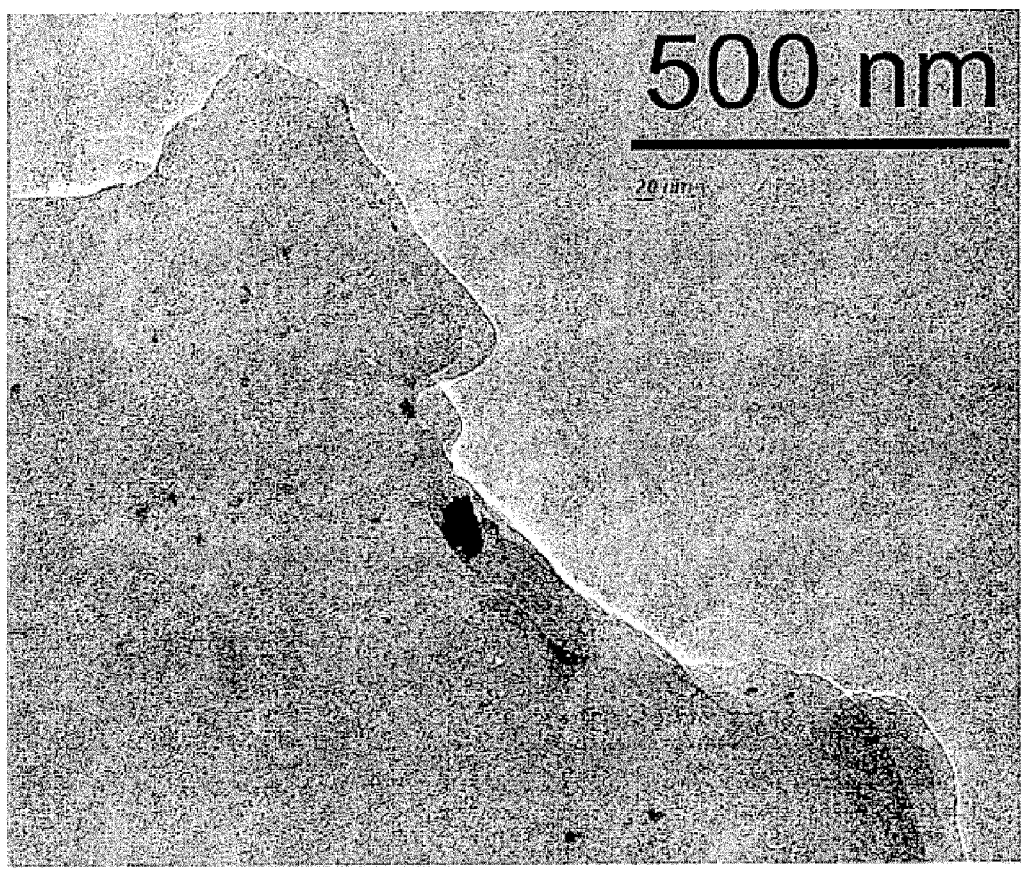

FIG. 2: Image obtained by transmission electron microscopy of a bacteriostatic composite material containing $2\times10^{-4}$ M of $Ag_2SO_4$ silver salt.

Figure 3:
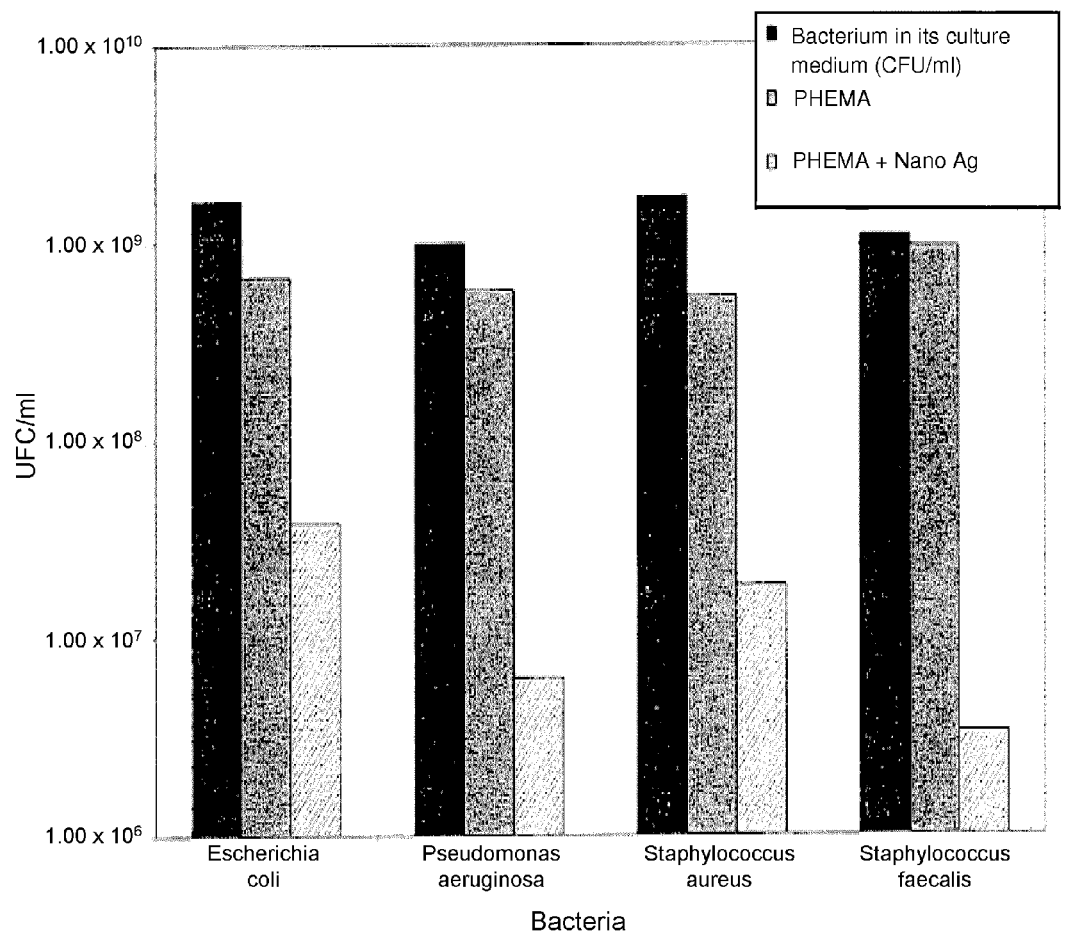

FIG. 3: Tests of a bacteriostatic material containing $2\times10^{-4}$ M of $Ag_2SO_4$ salt on four bacteria: *Escherichia coli, Pseudomonas aeruginosa, Staphylococcus aureus, Streptococcus faecalis*.

A solution comprising the following is prepared:

5 ml of $10^{-3}$ M $Ag_2SO_4$, 29.85 ml of HEMA, 3.73 ml of methanol, 1.49 ml of isopropanol and 9.93 ml of ultra-pure water at 18 Megohms. The products are mixed in a beaker and the final mixture is degassed for 10 minutes with argon in order to remove the oxygen gas. This operation, in the context of an industrial application, can be replaced, if necessary, by primary pumping to 1 mbar for 1 minute. The solution is then irradiated under gamma-rays with a dose of 2 kGray.

A bacteriostatic material with a final percentage by mass of silver of $3.1\times10^{-3}$% is obtained.

The same operation is repeated with a silver concentration of 0 M, $6\times10^{-5}$ M, $2\times10^{-4}$ M.

FIG. 1 shows an absorption spectrum obtained by difference between a bacteriostatic composite material containing a percentage by mass of $3.1\times10^{-3}$% of silver, in the form of nanoparticles, and an identical reference without silver nanoparticles.

The two absorption bands at 400 and 450 nm are characteristic of the silver nanoparticles.

The transmission electron microscopy characterizations made it possible to verify that the size of the nanoparticles was less than 10 nm (FIG. 2).

The effectiveness of the bacteriostatic composite material containing $Ag_2SO_4$ was tested on four bacteria: *Escherichia coli, Pseudomonas aeruginosa, Staphylococcus aureus, Streptococcus faecalis*. FIG. 3 shows the comparative change in the four bacteria after 24 hours of exposure to the material.

For a given bacterium, a preculture is prepared under sterile conditions in a 15 ml tube with 2 ml of suitable culture medium (see table), inoculated with 50 μl of a bacterial culture at saturation, and incubated for 12 h at 37° C. with shaking. One hundred microliters of this preculture are used to inoculate 20 ml of medium (identical to that used for the preculture) (inoculation at ½₀₀th). Two milliliters of this culture are distributed into each test or control tube; the test tubes contain 2 ml of gel+ the material prepared above with a final silver concentration of $2\times10^{-4}$ M (NanoAg on FIG. 3), and the control tubes contain 2 ml of gel; the tubes are placed at 37° C. for 12 h with shaking. After incubation, a turbidimetry measurement is carried out for each culture using a spectrophotometer, at a wavelength of 600 nm.

| Bacterium | Culture medium |
| --- | --- |
| *Escherichia coli* | LB |
| *Staphylococcus aureus* | LB |
| *Pseudomonas aeruginosa* | LB |
| *Streptococcus faecalis* | brain-heart |

Composition of the Culture Media

LB per liter: 10 g of tryptone, 10 g of yeast extract, 5 g of sodium chloride, adjusted to pH 7.4, autoclaved for 15 min at 121° C.

Brain-heart: per liter, 10 g of protease-peptone, 12.5 g of calf brain infusion, 5 g of bovine brain infusion, 2 g of glucose, 5 g of sodium chloride, 2.5 g of sodium hydrogen phosphate, adjusted to pH 7.4, autoclaved for 15 min at 121° C.

These tests show that 90% to 99% of the bacteria are destroyed in 24 hours.

By comparison, Ivan Sondi et al. (Journal of Colloid and Interface Science 275, 2004, 177-182) had to use a solution containing silver nanoparticles that was 1000 times more concentrated (20 μg/cm³) in order to obtain a similar result on the *Escherichia coli* bacterium.

The invention claimed is:

1. A method for producing a composite material comprising a porous polymer matrix in which silver nanoparticles are dispersed, this method comprising the following steps:
   (a) mixing two compositions in a solvent selected from the group consisting of water and at least one alcohol to form a mixture, wherein the compositions comprise:
      (i) a first composition comprising a polymerizable fluid comprising HEMA monomer, wherein the HEMA monomer is present in the polymerizable fluid composition in monomer form, and
      (ii) a second composition comprising silver salts,
   wherein the mixture comprises:
      58% to 63% by volume of HEMA monomer,
      5% to 10% by volume of methanol,
      1% to 5% by volume of isopropanol,
      15% to 25% by volume of water, and
      $10^{-1}$ to $10^{-5}$ percent by mass of silver salts; and
   (b) irradiating the mixture of step (a) with gamma radiation with a dose flow rate greater than or equal to 2 kGray/hour, that causes the simultaneous polymerization of the HEMA monomer and the formation of silver nanoparticles, thereby producing the composite material comprising a porous polymer matrix in which silver nanoparticles are dispersed.

2. The method as claimed in claim 1, in which the HEMA represents more than 50% by mass of the total mass of the monomers of the polymerizable fluid composition.

3. The method as claimed in claim 1, in which the composition comprising silver salts is an aqueous solution of silver salts.

4. The method as claimed in claim 1, in which the silver salts are chosen from the following list: $Ag_2SO_4$ and $AgNO_3$.

5. The method as claimed in claim 1, in which the mixture of step (a) also comprises between $10^{-6}$ and $10^{-3}$ M of at least one substance selected from the group consisting of poly (methyl methacrylate) (pMMA), polyvinyl-pyrrolidone, poly (acrylic acid) and polyacrylamide.

6. The method as claimed in claim 1, in which the mixture of step (a) is placed under an oxygen vacuum before irradiation.

7. The method as claimed in claim 1, in which the gamma radiation dose flow rate is from 2 to 30 kGray/hr.

8. The method as claimed in claim 1, in which the mixture of step (a) is introduced into a mold before irradiation.

* * * * *